(12) United States Patent
Ukaj

(10) Patent No.: US 7,958,588 B2
(45) Date of Patent: Jun. 14, 2011

(54) VARIABLE SPEED TOOTH POLISHING SYSTEM

(76) Inventor: Theresa Luz Ukaj, Pompano Beach, FL (US)

( * ) Notice: Subject to any disclaimer, the term of this patent is extended or adjusted under 35 U.S.C. 154(b) by 461 days.

(21) Appl. No.: 11/440,281

(22) Filed: May 24, 2006

(65) Prior Publication Data

US 2007/0136965 A1    Jun. 21, 2007

Related U.S. Application Data

(60) Provisional application No. 60/752,549, filed on Dec. 21, 2005.

(51) Int. Cl.
*A61C 1/16* (2006.01)
*A61C 3/06* (2006.01)

(52) U.S. Cl. ............... 15/28; 15/97.1; 433/116; 433/125

(58) Field of Classification Search .................... 15/22.1, 15/28, 97.1; 433/116, 125
See application file for complete search history.

(56) References Cited

U.S. PATENT DOCUMENTS

| | | | | |
|---|---|---|---|---|
| 1,694,636 A * | 12/1928 | Barker | ............................ | 15/110 |
| 2,039,278 A * | 5/1936 | Blanchard | ....................... | 15/188 |
| 3,195,537 A * | 7/1965 | Blasi | .............................. | 601/114 |
| 3,621,577 A * | 11/1971 | Spinello | ......................... | 433/166 |
| 3,939,599 A * | 2/1976 | Henry et al. | .................... | 433/99 |
| 4,274,173 A * | 6/1981 | Cohen | ................................ | 15/28 |
| 4,424,036 A * | 1/1984 | Lokken | ......................... | 433/116 |
| 5,131,846 A * | 7/1992 | Hall | ................................ | 433/116 |
| 5,380,202 A * | 1/1995 | Brahler | ......................... | 433/166 |
| 5,584,690 A * | 12/1996 | Maassarani | .................... | 433/125 |
| 5,642,995 A * | 7/1997 | Bailey | ........................... | 433/115 |
| 5,775,905 A * | 7/1998 | Weissenfluh et al. | ......... | 433/166 |
| 2006/0292522 A1* | 12/2006 | Lees et al. | ..................... | 433/116 |

* cited by examiner

*Primary Examiner* — Randall Chin
(74) *Attorney, Agent, or Firm* — Gold & Rizvi, P.A.; H. John Rizvi; Glenn E. Gold

(57) ABSTRACT

A variable speed tooth polishing system including a tooth polisher with multiple polishing head capability, in order to provide therapeutic treatment to gums and guard against undesired exposure to potentially hazardous fluids present during routine dental cleansing and polishing, such as polishing paste, tooth paste, blood, and salivary excretions.

11 Claims, 4 Drawing Sheets

VARIABLE SPEED TOOTH POLISHING SYSTEM

CROSS-REFERENCE TO RELATED APPLICATION

This application claims the benefit of co-pending U.S. Provisional Patent Application Ser. No. 60/752,549, filed Dec. 21, 2005, which is incorporated herein in its entirety.

BACKGROUND OF THE INVENTION

1. Field of the Invention

The present invention relates generally to a variable speed tooth polishing system containing two polishing heads for added stability on the teeth, that can be used to massage the gums, while at the same time providing hygienic protection against the mess created by the spraying of fluids during dental cleaning, such as polishing paste, tooth paste, saliva, and blood.

2. Description of the Prior Art

Oral disease has plagued human beings since the beginning of history, but it wasn't until dentistry advanced to the stage of detecting bacteria responsible for periodontal disease, that preventive dentistry became important. Detecting bacteria was further fueled by public concern regarding the risks of contracting infectious diseases through dental procedures, which in turn, has created an increased awareness and desire for more sophisticated dental equipment to better maintain teeth, for health, as well as aesthetic reasons.

Existing dental cleaners and polishers, however, are not without their disadvantages. To begin with, current polishers usually provide just one polishing head. This type of configuration has a tendency of rendering the polishers unstable, as they do not get adequate hold on the teeth and gums during the vibrating created by the rotating motion of the motor.

Furthermore, the bulkiness of existing polisher heads is not very comfortable when inserted into the mouth, limiting access to hard to reach teeth. This discomfort can lead to a shortened amount of cleansing and polishing time because of the user's inability to endure the process for extended lengths of time, which in turn results in deficient dental hygiene.

Moreover, standard polishers tend to have a power switch, which activates rotation at one particular speed. This is especially troublesome in situations where less force is required, as in the case of a child, or higher speeds are necessitated, by adults with more serious cleaning issues.

Additionally, current polishers do not provide adequate protection from the risks of potentially infectious fluids emanating from the patients mouth. As a result, users are exposed to such potentially harmful materials as saliva, blood, pastes, and other dental waste materials.

Another disadvantage of existing polishers is the inability of the polishing heads to remove food particles from between the teeth and gums. This is an important concern because a leading cause of periodontal disease is lack of flossing, which leads to plaque deposits and tooth decay.

Yet another disadvantage of standard polishers is that they concentrate on the teeth alone. Since the health of gums is just as important as the teeth themselves, overlooking care to this area can also lead to serious dental health issues that should be addressed as part of any preventative regimen.

Finally, existing polishers do not offer the option of interchangeable prophy angles. Because of this, users with various needs not addressed by a specific polishing device are forced to utilize multiple prophy angles, if they desire to receive optimum results, both hygienically and aesthetically.

Accordingly, there is an established need for a variable speed tooth polishing system that, in addition to being constructed in a smaller, more adaptable manner, also provides safeguards against infectious materials and unhygienic messes, and which contains multiple polishing brushes that provide a firmer, more efficient grip on the teeth during the dental cleaning/polishing procedure.

SUMMARY OF THE INVENTION

The present invention is directed to a variable speed tooth polishing system. The tooth polisher of the present invention is configured for facilitating dental care by incorporating a more practical size, shape, and functionality into a simple to use mechanism, which takes into consideration aesthetic, as well as hygienic issues.

An object of the present invention is to provide a variable speed tooth polishing system that utilizes a multi-brush system.

A further object of the present invention is to provide a variable speed tooth polishing system that provides the proper amount of protection against exposure to adverse materials.

Another object of the present invention is to provide a variable speed tooth polishing system that massages the gums, while simultaneously buffing teeth for a more aesthetically pleasing appearance.

In accordance with a first aspect of the invention, a variable speed tooth polishing system is provided comprising a prophy angle containing dual polishers that can be used in unison, or individually.

In accordance with a second aspect of the invention, a splatter guard is provided that encases the polishers, in order to prevent users from being exposed to unsanitary byproducts during the dental cleaning procedure.

In accordance with a third aspect of the invention, therapeutic massage is rendered to the gums by means of the polishers, promoting dental health and well-being.

In accordance with a fourth aspect of the invention, the unique prophy angle polisher of the variable speed tooth polishing system is capable of being separated from the hand grip and utilized with other motorized dental cleaning aids.

In accordance with a fifth aspect of the invention a variable speed tooth polishing system is provided with multi-speed capability, in order to address the individual needs of users who require minimum, medium, or maximum rotational force of the polishers.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION OF THE PREFERRED EMBODIMENTS

Shown throughout the figures, the present invention is generally directed towards a variable speed tooth polishing system, designed specifically to provide users with a practical and efficient means for practicing dental hygiene in a compact, flexible structure that takes into consideration dental aesthetics, gum maintenance, and minimization of contact with potentially infectious substances.

Figure 1:
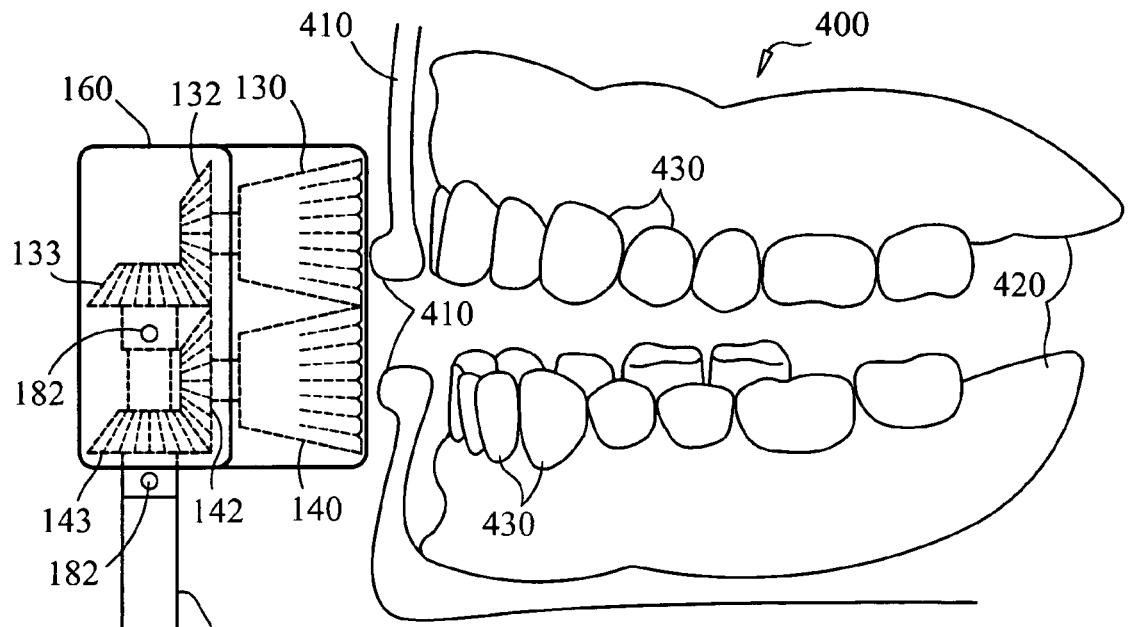
FIG. 1 is a left side view of the variable speed tooth polishing system, depicting the prophy angle, polisher, inner gears, before it is placed in the mouth.
Figure 2:
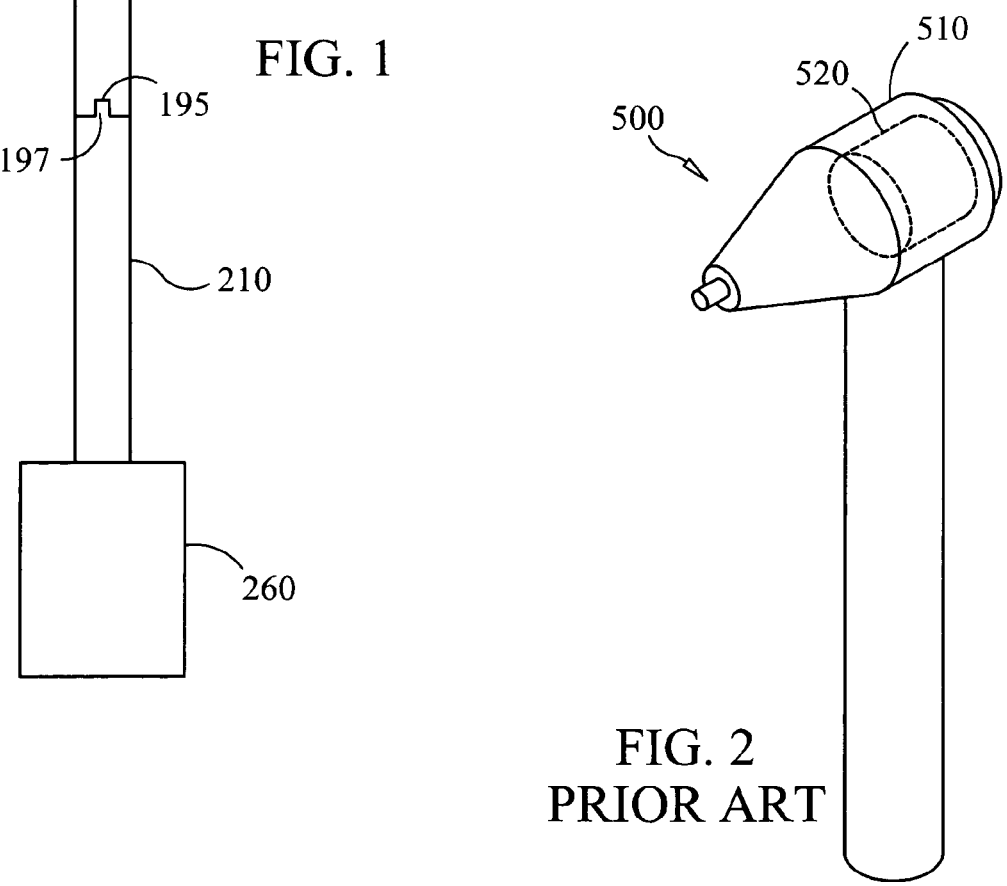
FIG. 2 is a front perspective view of a prior art polisher.
Figure 3:
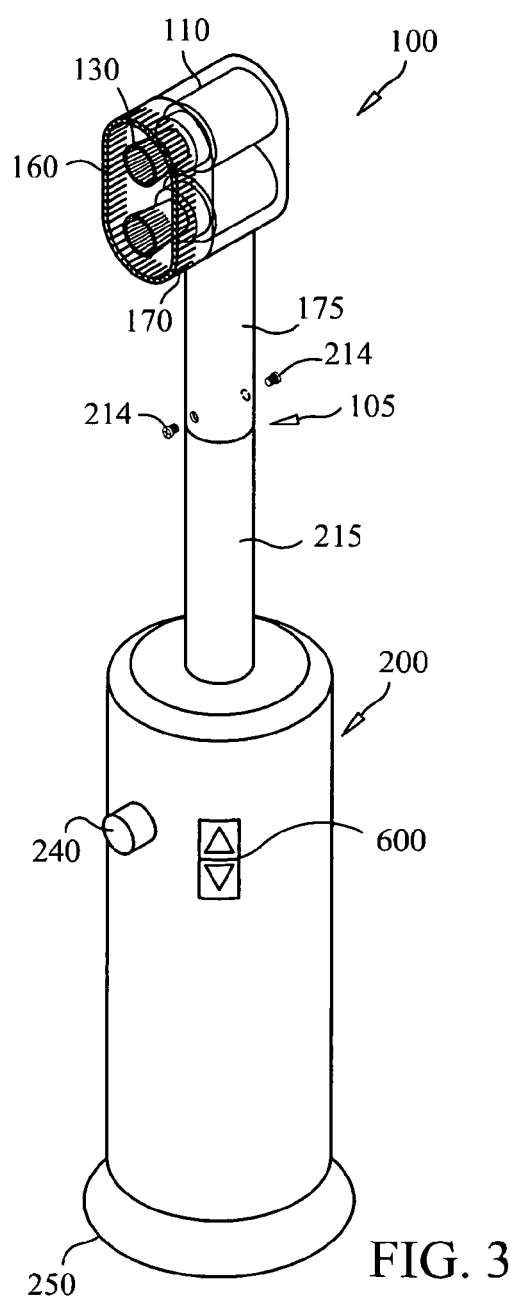
FIG. 3 is a front perspective view of a variable speed tooth polishing system with the prophy angle attached.

Referring now to FIGS. 1 and 3, a prophy angle 105 of a variable speed tooth polishing system 100 is shown before it has been inserted into the mouth 400, past the lips 410 in order to make contact with the gums 420 and teeth 430. The prophy angle 105 includes are a first polisher 130, a first polisher gear 132, a first drive gear 133, a second polisher 140, a second polisher gear 142, a second drive gear 143, and a splatter guard 160. Referring briefly to FIG. 2, the prior art prophy angle 500 includes a polisher head 510, which contains within its structure a polisher motor 520. The prophy angle 105 may be secured to a polisher hand grip 200 by threading at least one set screw 214 through the prophy angle connector housing 175 into a hand grip connector housing 215. These screws 214 will "preferably" be made of a non-corrosive material, such as plastic.

Figure 4:
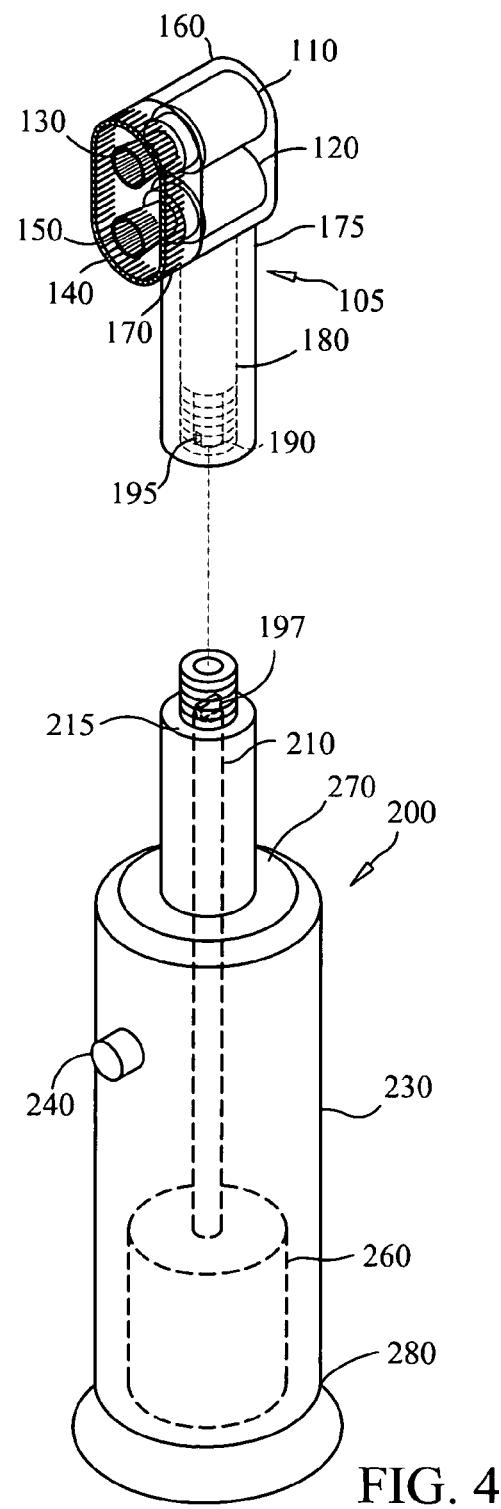
FIG. 4 is a partially exploded front perspective view of a variable speed tooth polishing system with a prophy angle removed from a hand grip.

Referring now to FIG. 4, the variable speed tooth polishing system 100 is shown with the prophy angle 105 separated from a polisher hand grip 200. The prophy angle 105 includes a prophy angle connector housing 175 and the polisher hand grip 200 includes a hand grip connector housing 215. The prophy angle 105 is connected to the hand grip connector housing 215 by screwing the hand grip connector housing 215 into the prophy angle connector housing 175. The prophy angle shaft 180 includes a drive slot 195, which is sized to receive a drive tongue 197 extending from an end of a hand grip connector shaft 210. The hand grip connector shaft 210 extends from a motor 260. The first and second drive gears are attached to the prophy angle shaft 180 with set screws 182 or the like.

It will be appreciated by those skilled in the art that these structural elements of the present invention may be formed out of natural and synthetic materials, such as plastic, rubber, and combinations thereof, or any of a wide variety of other known materials without departing from the present invention. The figures illustrate the use of threads to connect the prophy angle 105 to the polisher hand grip 200, but may include any suitable removable assembly method, such as any type of fastener.

Also illustrated in the figures is a more detailed view of the prophy angle 105, showing the first polisher 130 inserted into a first polisher housing 110 and a second polisher 140 inserted into the second polisher housing 120. Both the first polisher 130 and the second polisher 140 include a plurality of polisher slots 150 to enable more stable and thorough contact with the teeth 430 and gums 420. The first and second polishers are preferably fabricated from a flexible material. A splatter guard 160 surrounds the first polisher 130 and the second polisher 140. A plurality of splatter slots 170 are formed around a perimeter of the splatter guard 160. The splatter guard 160 is preferably fabricated from a flexible material. It is preferable that the plurality of splatter slots 170 are 5 mm to 7 mm long, but could be any suitable length. The plurality of polisher slots 150 are preferably no more than 3 mm in length.

The polisher hand grip 200 includes a hand grip body 230, a power button 240, the motor 260, a hand grip top portion 270 and a handgrip bottom portion 280. The hand grip top portion 270 terminates a top of the hand grip body 230 and the handgrip bottom portion 280 terminates a bottom of the hand grip body 230. The motor 260 is retained in the hand grip body 230. The power button 240 controls the flow of electrical power to the motor 260. When the motor 260 is activated by the power button 240, the hand grip connector shaft 210 revolves, which turns the prophy angle shaft 180. Rotation of the prophy angle shaft 180 causes the first and second drive gears to rotate the first and second polisher gears, respectively. Spinning of the first and second polishers polishes the teeth 430 and massages the gums 420. The polisher hand grip 200 also contains the hand grip speed control 600, which regulates the rotational speed.

Figure 5:
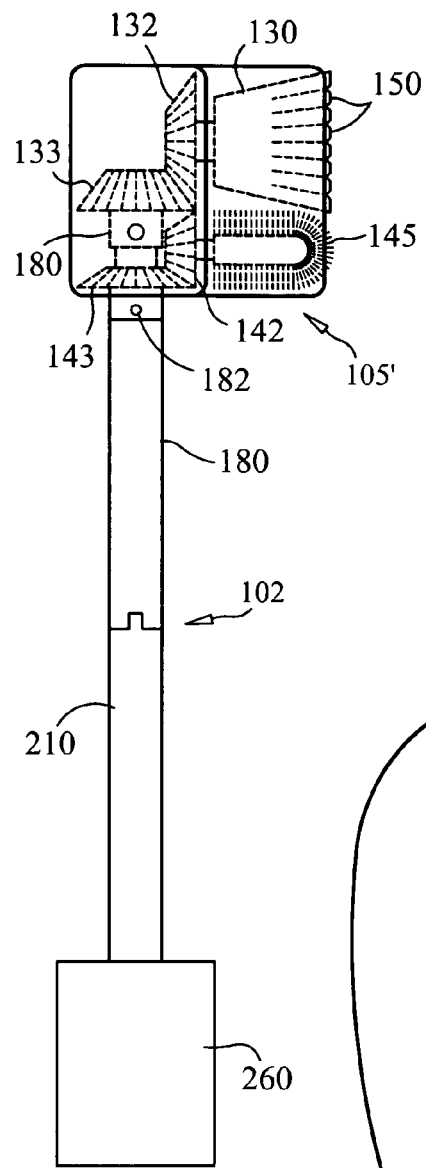
FIG. 5 is a left side view of a second embodiment of a variable speed tooth polishing system showing, wherein one polisher is replaced with a brush.

Referring now to FIG. 5, a second embodiment of a variable speed tooth polishing system 102 is shown with the second polisher 140 replaced by a polisher brush 145. It will be appreciated by those skilled in the art that the prophy angle 105' of the variable speed tooth polishing system 102 can be attached to other polisher hand grips, and that the first polisher 130 and the second polisher 140 can be removed and either act alone in order to access hard to reach teeth, or be replaced with other variations besides the polisher brush 145, without deviating from the present invention. Another alternative embodiment would entail the first polisher 130 and the second polisher 140 having a plurality of bristles, like those of a toothbrush, or a wide variety of other polishing means without departing from the present invention.

Figure 6:
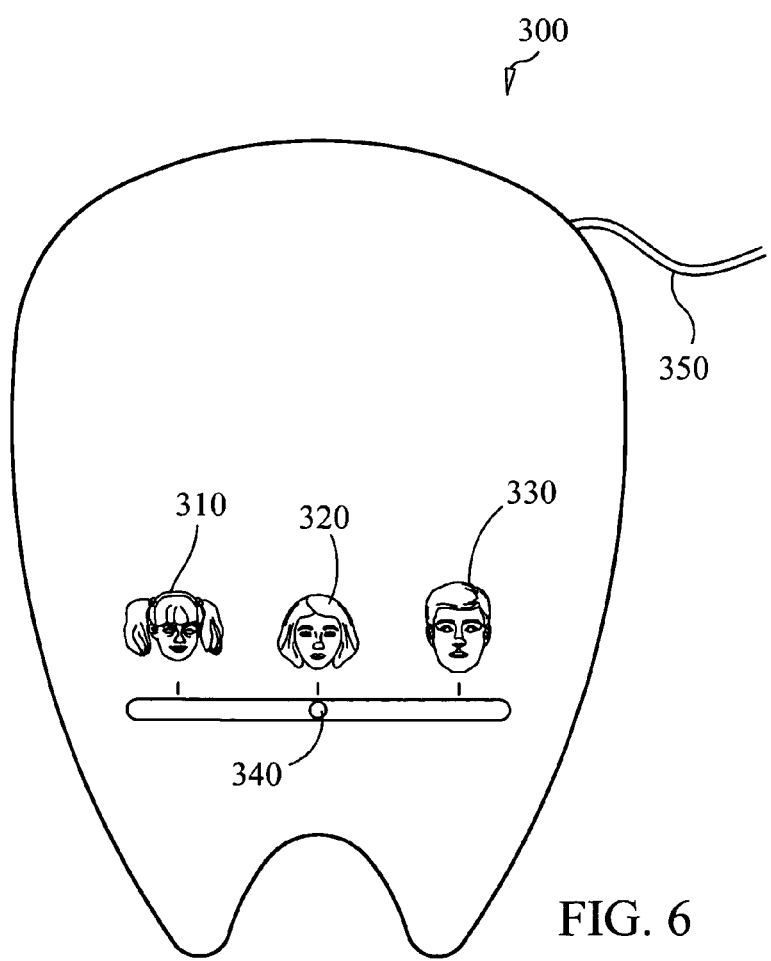
FIG. 6 is a front view of a control unit depicting variable speed input, as well as a wire that connects the control unit to a polisher hand grip.

FIG. 6 illustrates a control unit 300 of the variable speed tooth polishing system 100, 102. The control unit 300 determines the rotational speed of the first polisher 130 and second polisher 140 by movement of an indicator switch 340 to either the first setting indicator 310 (low speed), the second setting indicator 320 (medium speed), or the third setting indicator 330 (high speed). It is attached to the polisher hand grip 200 via a wire 350.

Figure 7:
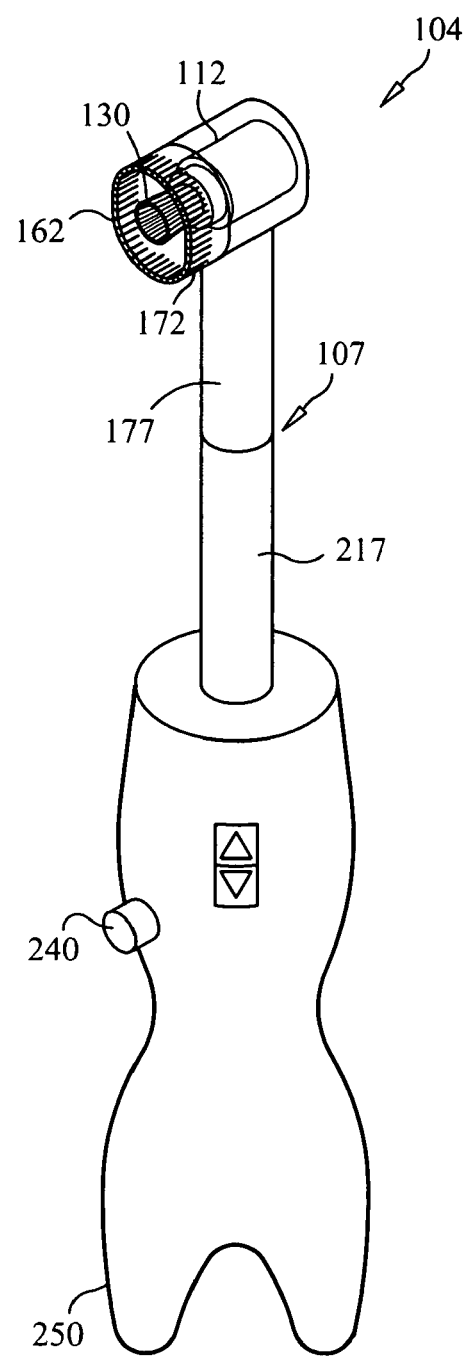
FIG. 7 is a perspective view of a third embodiment of a variable speed tooth polishing system with a single polisher.

FIG. 7 illustrates a third embodiment of a variable speed tooth polishing system 104 with a single polisher 130. The variable speed tooth polishing system 104 includes a polisher hand grip 250 and a prophy angle 107. A hand grip connector housing 217 extends from the polisher hand grip 250. The prophy angle 107 includes a prophy angle connector housing 177 and a splatter guard 162. The prophy angle connector housing 177 is preferably screwed to the hand grip connector housing 217, but other attachment methods may also be used. A polisher housing 112 is retained in the splatter guard 162. A plurality of splatter slots 172 are formed in a front of the splatter guard 162. The polisher is retained in the polisher housing 112.

Figure 8:
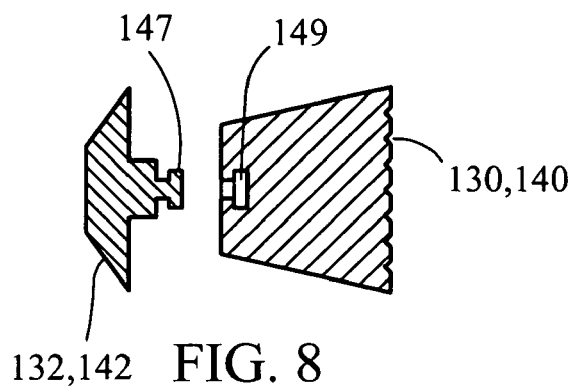
FIG. 8 is a cross-sectional view of a bevel gear having an undercut projection and a polisher having an undercut cavity for receiving the undercut projection of a variable speed tooth polishing system.
Figure 9:
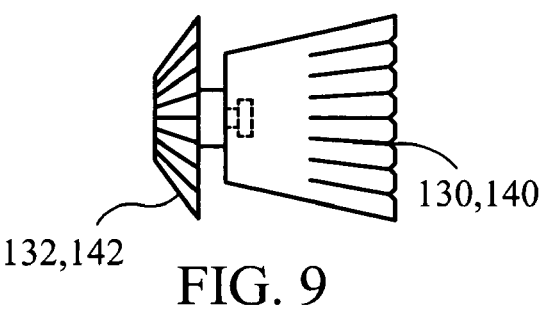
FIG. 9 is a cross-sectional view of a bevel gear having an undercut projection and a polisher having an undercut cavity for receiving the undercut projection assembled together of a variable speed tooth polishing system.
Figure 10:
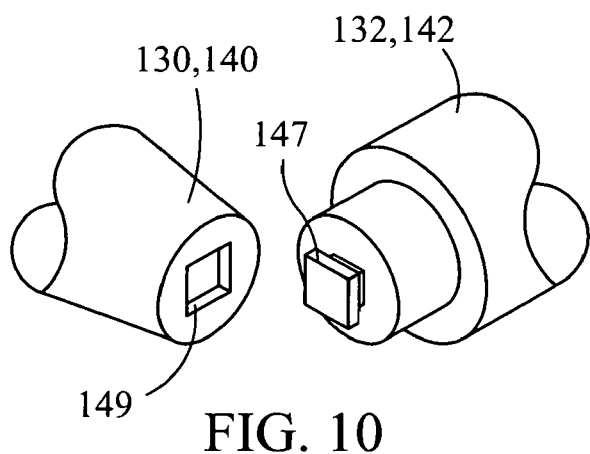
FIG. 10 is an enlarged perspective view of an undercut projection and an undercut cavity for receiving the undercut projection adjacent to each other of a variable speed tooth polishing system.

FIGS. 8-10 illustrate a method of attaching a polisher 130, 140 to a polisher gear 132, 142, respectively. An undercut projection 147 extends from the polisher gear 132, 142. A projection cavity 149 is formed in a rear of the polisher 130, 140. The projection cavity 149 is sized to receive insertion of the undercut projection 147. After insertion of the undercut projection 147, the polisher 130, 140 is turned 45 degrees relative to the polisher gear 132, 142 to retain thereof relative to each other. However, other methods of removably attaching the polisher 130, 140 to the polisher gear 132, 142 may also be used.

Since many modifications, variations, and changes in detail can be made to the described preferred embodiments of the invention, it is intended that all matters in the foregoing description and shown in the accompanying drawings be interpreted as illustrative and not in a limiting sense.

I claim:

1. A variable speed tooth polishing system comprising:
   at least one polisher;
   a prophy angle engaged with said at least one polisher for rotatably retaining said at least one polisher;
   a splatter guard being formed as a continuous wall encompassing said at least one polisher;
   a plurality of axial serrations being formed about a perimeter of said splatter guard, said plurality of axial serrations are cut through a wall of said splatter guard, said serrations starting at an open end of said splatter guard and continuing into a length of said splatter guard forming a series of flexible splatter guard fingers about said open end which entrap any loose material resulting from a polishing process within the splatter guard; and
   a power source for rotating said at least one polisher.

2. The variable speed tooth polishing system of claim 1, further comprising:
   a control unit for varying the speed of said power source.

3. The variable speed tooth polishing system of claim 1, further comprising:
   a hand grip; and
   said prophy angle being removable from said hand grip.

4. The variable speed tooth polishing system of claim 3 wherein:
   said power source being retained in said hand grip.

5. The variable speed tooth polishing system of claim 3, further comprising:
   a prophy angle shaft extending from said prophy angle; and
   a hand grip connector shaft extending from said hand grip, said prophy angle shaft being engagable with said hand grip connector shaft.

6. A variable speed tooth polishing system comprising:
   a prophy angle connector housing;
   a prophy angle shaft extending from a prophy angle;
   at least one polisher, each said at least one polisher attached to a drive gear, wherein said drive gear is operably engaged with said prophy angle shaft at a right angle to rotate each said at least one polisher;
   a splatter guard being formed as a continuous wall encompassing said at least one polisher and fixedly attached to said prophy angle housing;
   a plurality of axial serrations being formed about a perimeter of said splatter guard, said plurality of axial serrations are cut through a wall of said splatter guard, said serrations being formed about a perimeter of said splatter guard, said plurality of axial serrations starting at an open end of said splatter guard and continuing into a length of said splatter guard forming a series of flexible splatter guard fingers about said open end which entrap any loose material resulting from a polishing process within the splatter guard; and
   a power source operationally engaged with said prophy angle shaft for rotating said at least one polisher.

7. The variable speed tooth polishing system of claim 6, wherein:
   said splatter guard is provided in an oval shape.

8. The variable speed tooth polishing system of claim 7, wherein:
   said splatter guard remains stationary whereas said at least one polisher rotates.

9. The variable speed tooth polishing system of claim 6, further comprising:
   said at least one polisher comprising a first polisher positioned adjacent to a second polisher;
   a second drive gear attached to said prophy angle shaft, wherein said second drive gear is operably engaged with said prophy angle shaft at a right angle to rotate said second polisher; and
   the splatter guard being formed as a continuous wall encompassing said first and second polishers.

10. The variable speed tooth polishing system of claim 9, wherein:
    said splatter guard is provided in an oval shape.

11. The variable speed tooth polishing system of claim 9, wherein:
    said first polisher is fabricated having a first shape said second polisher is fabricated having a second shape, wherein said first shape is different from said second shape.

* * * * *